United States Patent [19]

Narisada

[11] 4,139,711
[45] Feb. 13, 1979

[54] DIHYDROETHANOANTHRACENE DERIVATIVES

[75] Inventor: Masayuki Narisada, Ibaraki, Japan

[73] Assignee: Shionogi & Co., Ltd., Osaka, Japan

[21] Appl. No.: 767,633

[22] Filed: Feb. 10, 1977

Related U.S. Application Data

[62] Division of Ser. No. 692,941, Jun. 4, 1976, Pat. No. 4,061,854.

[30] Foreign Application Priority Data

Jun. 12, 1975 [JP] Japan .................................. 50-71645
Jun. 12, 1975 [JP] Japan .................................. 50-71646

[51] Int. Cl.$^2$ ..................... C07C 93/20; C07C 93/00
[52] U.S. Cl. .......................................... 560/8; 424/299
[58] Field of Search ............................. 560/8; 260/469

[56] References Cited

U.S. PATENT DOCUMENTS 2,673,874  3/1954  Jenkins ................................. 260/469

FOREIGN PATENT DOCUMENTS 1550109  11/1968  France.

*Primary Examiner*—Jane S. Myers
*Attorney, Agent, or Firm*—Wenderoth, Lind & Ponack

[57] ABSTRACT

Dihydroethanoanthracene derivatives of the formula:

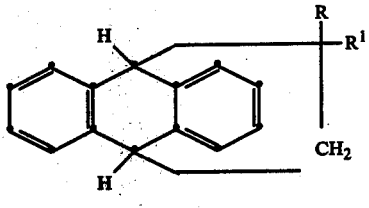

[wherein R represents a hydrogen or $C_1$-$C_4$ alkyl; $R^1$ represents a group

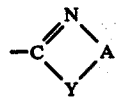

(in which A represents a $C_2$-$C_4$ alkylene optionally substituted by one or two $C_1$-$C_4$ alkyls or by a phenyl; and Y represents an oxygen, sulfur, or imino) or group

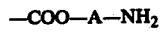

(in which A is as defined above)] and their pharmaceutically acceptable acid addition salts, being useful as antidepressants or their synthetic intermediates.

5 Claims, No Drawings

DIHYDROETHANOANTHRACENE DERIVATIVES

The present application is a divisional of application Ser. No. 692,941, filed June 4, 1976, now U.S. Pat. No. 4,061,854.

The present invention relates to dihydroethanoanthracene derivatives and their pharmaceutically acceptable acid addition salts being useful as antidepressants or their synthetic intermediates. More particularly, this invention relates to dihydroethanoanthracene derivatives of the formula:

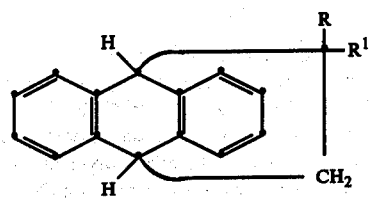

[wherein R represents a hydrogen or $C_1$-$C_4$ alkyl; and $R^1$ represents a group

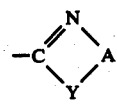

(in which A represents a $C_2$-$C_4$ alkylene optionally substituted by one or two $C_1$-$C_4$ alkyls or by a phenyl; and Y represents an oxygen, sulfur, or imino) or group

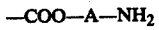

(in which A is as defined above)] and their pharmaceutically acceptable acid addition salts.

In said definition, the alkyl involves methyl, ethyl, propyl, isopropyl, butyl, and isobutyl, and the alkylene involves ethylene, trimethylene, and tetramethylene.

The dihydroethanoanthracene derivatives (I) can be prepared by reacting a nitrile of the formula:

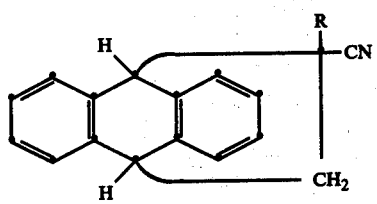

[wherein R is as defined above] with an amine of the formula:

[wherein A and Y each is as defined above] to give a cyclic imine of the formula:

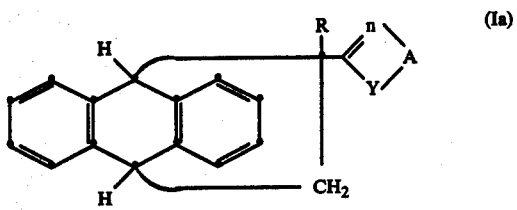

[wherein A, R, and Y each is as defined above]; or hydrolyzing the cyclic imine, when Y is oxygen, to give an ester of the formula:

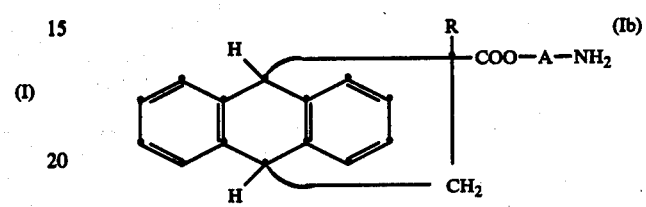

[wherein A and R each is as defined above].

The preparation of the dihydroethanoanthracene derivatives (I) is shown in the following scheme:

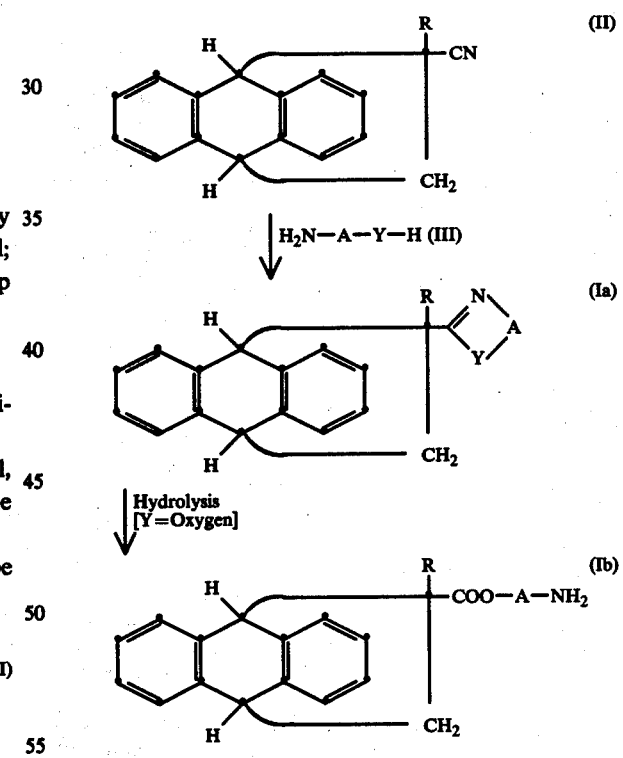

[wherein A, R, and Y each is as defined above].

Accordingly, the dihydroethanoanthracene derivatives (I) can be prepared in two steps. At first, the reaction of the nitrile (II) with the amine (III) is carried out under heating, if necessary, in the presence of a suitable accelerator (e.g. zinc chloride, zinc acetate, aluminum chloride, hydrogen sulfide). A suitable inert solvent (e.g. benzene, toluene, xylene, dioxane, halobenzene) may be added, if necessary. Thus obtained cyclic imine (Ia) is occasionally converted into suitable organic or inorganic acid addition salts (e.g. hydrochloride, nitrate, acetate, succinate, methanesulfonate). The cyclic imine (Ia) is prepared in a mixture of stereoisomers, depending on the sort of the starting nitrile (II) and amine (III), and the isomers may be purified in a form of mixture or be resoluted into individual isomers in a conventional manner.

Secondly, the hydrolysis of the cyclic imine (Ia), when Y is oxygen, is carried out by treating with at least one mol equivalent of an aqueous acid (e.g. hydrochloric acid, sulfuric acid, nitric acid) at room temperature or under cooling or heating. If necessary, a suitable solvent (e.g. water, alcohols, dioxane) may be used. Thus-obtained ester (Ib) can be collected either in a form of a salt of the acid above used or in a form of free amine by treating said salt with a suitable base (e.g. sodium bicarbonate, ammonia, pyridine). So, the salt can be converted into a salt of another acid such as organic acid (e.g. succinic acid, acetic acid, methanesulfonic acid).

The starting nitrile (II) can be prepared by reacting anthracene with an acrylonitrile (IV), as shown in the following scheme:

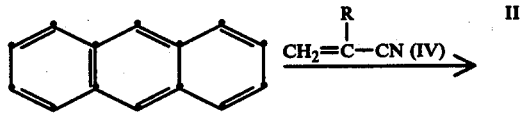

[wherein R is as defined above].

The objective dihydroethanoanthracene derivatives (I) involves the cyclic imine (Ia) and ester (Ib). These dihydroethanoanthracene derivatives (I) and their pharmaceutically acceptable acid addition salts are useful as antidepressants or their synthetic intermediates, showing an excellent central nervous activity, in particular antiptotic activity against reserpine. For example, 2-aminoethyl 9,10-dihydro-9,10-ethanoanthracene-11-carboxylate hydrochloride showed $ED_{50}$ 30 mg/kg (mouse, per os) with $LD_{50}$ 902 mg/kg; and 11-(2-oxazolin-2-yl)-9,10-dihydro-9,10-ethanoanthracene showed $ED_{50}$ 41 mg/kg (mouse, per os) in the antiptotic activity against reserpine with $LD_{50}$ 3536 mg/kg. The other objective compounds (I) showed similar pharmacological activities.

The dihydroethanoanthracene derivatives (I) and their pharmaceutically acceptable acid addition salts are applied singly or in combination with pharmaceutically suitable carriers such as wheat starch, corn starch, potato starch, gelatin, water etc. The choice of carriers is determined by the preferred route of administration, the solubility of the substance, and standard pharmaceutical practice. Examples of pharmaceutical preparations are tablets, capsules, pills, suspensions, syrups, powders, and solutions. These compositions can be prepared in a conventional manner. A suitable dosage of the dihydroethanoanthracene derivatives (I) or their pharmaceutically acceptable acid addition salts for adults is in the order of about 15 to 750 mg/day.

Presently-preferred and practical embodiments of the present invention are illustratively shown in the following examples.

EXAMPLE 1

(1) A mixture of 11-cyano-9,10-dihydro-9,10-ethanoanthracene (4.6 g), ethanolamine (1.8 g) and zinc acetate (250 mg) is stirred at 130° C. for 5 hours. The reaction mixture is dissolved in benzene and passed through a column of 10% hydrated alumina. The eluate is evaporated to remove the solvent, and the residue is recrystallized from ether to give 11-(2-oxazolin-2-yl)-9,10-dihydro-9,10-ethanoanthracene (3.3 g) as crystals melting at 155 to 156° C. IR (KBr), 1655 cm$^{-1}$ (O—C≡N).

(2) A solution of 11-(2-oxazolin-2-yl)-9,10-dihydro-9,10-ethanoanthracene (4.122 g) in 1.074 N hydrochloric acid (13.9 ml) is allowed to stand at room temperature for 2.5 hours. The reaction mixture is mixed with dioxane to dissolve the precipitate formed and evaporated at room temperature under reduced pressure to remove the solvent. The residue is recrystallized from anhydrous ethanol-ether to give 2-aminoethyl 9,10-dihydro-9,10-ethanoanthracene-11-carboxylate hydrochloride ¼ hydrate (4.641 g) as crystals melting at 155 to 158° C. IR (Nujol), 3379, 1735 cm$^{-1}$.

EXAMPLE 2

A mixture of 11-cyano-9,10-dihydro-9,10-ethanoanthracene (4.6 g), ethylenediamine (1.5 g) and hydrogen sulfide (about 100 mg) is stirred at 130° C. for 20 hours. The reaction mixture is mixed with water and ether to be distributed in two layers. The ether layer is washed with water, dried, and evaporated to remove the ether. The residue is recrystallized from ether to give 11-(2-imidazolin-2-yl)-9,10-dihydro-9,10-ethanoanthracene (5.0 g) as crude crystals. IR (KBr), 1621 cm$^{-1}$ (N—C≡N).

EXAMPLE 3

A mixture of 11-cyano-9,10-dihydro-9,10-ethanoanthracene (4.6 g) and 2-aminoethanethiol (2.0 g) is stirred at 130° C. for 4 hours. The reaction mixture is recrystallized from ethanol to give 11-(2-thiazolin-2-yl)-9,10-dihydro-9,10-ethanoanthracene (4.5 g) as crystals melting at 160 to 161° C. IR (KBr), 1619 cm$^{-1}$ (S—C≡N).

EXAMPLES 4-9

Using the starting materials (II) and (III), the reactions each is carried out as in Example 1 (1), whereby the corresponding products (Ia) are obtained.

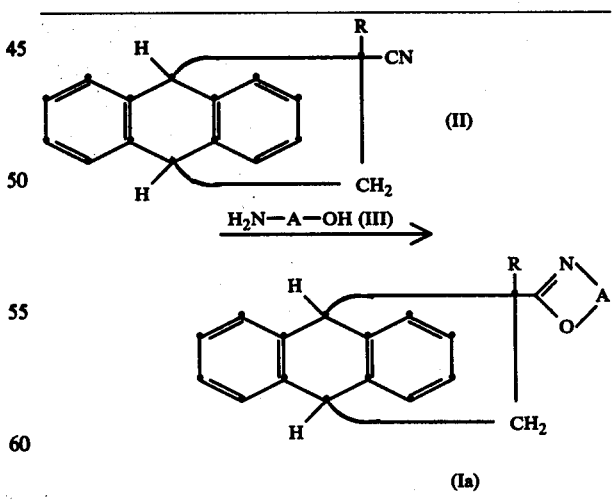

| Ex. No. | II R | III A | Ia m.p. (° C.) | IR (cm$^{-1}$) |
|---|---|---|---|---|
| 4 | H | Me<br>—C—CH$_2$—<br>Me | 190-191 | 1656 (CHCl$_3$) |

-continued

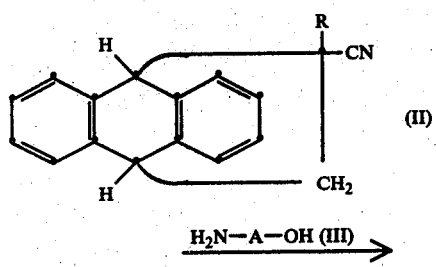

H₂N—A—OH (III) →

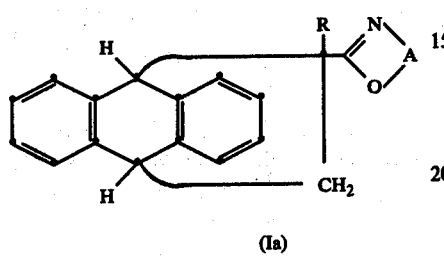

| Ex. No. | II R | III A | m.p. (° C.) | IR (cm⁻¹) |
|---|---|---|---|---|
| 5 | H | —CH₂CH— (Me) | 118–120[a] | 1658 (CHCl₃) |
| 6 | H | —CH—CH₂— (Me) | 187–189[b] | 1655 (CHCl₃) |
|   | H | " | 116.5–118[c] | 1659 (CHCl₃) |
| 7 | H | —CH₂CH— (Ph) | 150–151[d] | 1664 (Nujol) |
|   | H | " | 115–117[e] | 1652 (Nujol) |
| 8 | Me | —(CH₂)₂— | 129–134 | 1654 (CHCl₃) |
| 9 | H | —(CH₂)₃— | 165–169 | 1673, 1660.5 (CHCl₃) |

Note:
The abbreviations in the table each has the following significance:

H (Hydrogen);

Me (Methyl group);

Ph (Phenyl group);

m.p. (Melting point);

IR (Infra red absorption spectre);

[a] a mixture of diastereoisomers;

two combinations [b,c] and [d,e], other diastereoisomers respectively.

EXAMPLES 10–11

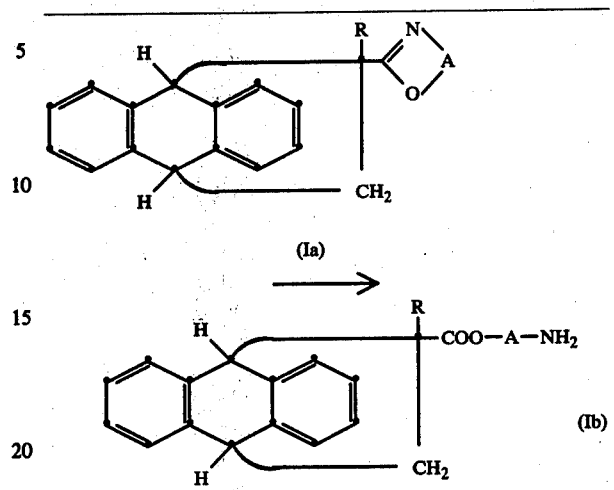

| Ex. No. | R | Ia —O—A—N= | m.p. (° C.) | Ib IR (cm⁻¹) |
|---|---|---|---|---|
| 10 | H | —CH—CH₂— (Me) | 169–171 (HCl) | 1726 (Nujol) |
| 11 | CH₃ | —CH₂—CH₂— | 190–193 (HCl) | 1737 (CHCl₃) |

Note:
The abbreviations each is as defined above.

What is claimed is:

1. A member selected from the group consisting of a compound of the formula

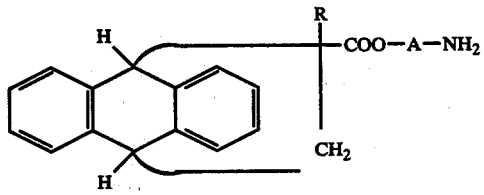

wherein R represents hydrogen or C₁–C₄ alkyl, and A represents a member selected from the group consisting of C₂–C₄ alkylene and C₂–C₄ alkylene substituted by one or two C₁–C₄ alkyl moieties or by phenyl, and a pharmaceutically acceptable acid addition salt thereof.

2. A compound according to claim 1 wherein R is hydrogen and A is C₂–C₃ alkylene.

3. A compound according to claim 1, namely 2-aminoethyl 9,10-dihydro-9,10-ethanoanthracene-11-carboxylate.

4. A compound according to claim 1, namely 2-aminoethyl 11-methyl-9,10-dihydro-9,10-ethanoanthracene-11-carboxylate.

5. A compound according to claim 1, namely 1-methyl-2-aminoethyl 9,10-dihydro-9,10-ethanoanthracene-11-carboxylate.

* * * * *